United States Patent [19]

Hsiung et al.

[11] Patent Number: 5,122,461
[45] Date of Patent: Jun. 16, 1992

[54] PREPARATION OF PYROCATECHOLIC COMPOUNDS

[75] Inventors: Kuang-Pin Hsiung, Hsinchu; Feng-Tsun Lee, Taipei Hsien; Chung-Long Hsieh, Hsinchu, all of Taiwan

[73] Assignee: Industrial Technology Research Institute, Taiwan, Taiwan

[21] Appl. No.: 615,604

[22] Filed: Nov. 19, 1990

[51] Int. Cl.$^5$ .................. C12P 13/04; C12P 13/22; C12P 9/00; C12N 9/02

[52] U.S. Cl. .................. 435/106; 435/108; 435/117; 435/120; 435/121; 435/122; 435/123; 435/125; 435/126; 435/128; 435/131; 435/142; 435/146; 435/156; 435/189

[58] Field of Search .............. 435/108, 189, 156, 108, 435/146, 142, 106, 117, 120, 121, 122, 123, 125, 126, 128, 131

[56] References Cited

U.S. PATENT DOCUMENTS 2,956,929  10/1960  Cohen et al.
3,386,888  6/1968   Chibata et al.
3,669,837  6/1972   Parcell
3,671,397  6/1972   Sih
3,674,767  7/1972   Lilly et al.
3,791,924  2/1974   Ogata et al. .................. 435/108
3,812,009  5/1974   Semersky

OTHER PUBLICATIONS

Wykes, J. R. et al. Nature 230: 1971, p. 187.
Evans, W. C. et al. Biochem. J. 31: 1937, pp. 2162-2170.
Evans, W. C. et al. Biochem. J. 31: 1937, pp. 2155-2161.
Podila, G. K., biochem, Biophys. Res. Commun. 141:697 (1986).
Leadlay, P. F., The Chemical Society Monograph for Teachers No. 32, 67 (1978).
Findeis, M. A. et al., Ann. Rep. in Med. Chem. 19, 263 (1984).

Primary Examiner—Herbert J. Lilling
Attorney, Agent, or Firm—Darby & Darby

[57] ABSTRACT

The invention relates to a novel method for preparing pyrocatecholic compounds from monophenolic compounds using catalysis by monophenol monooxygenase in an aqueous solution containing metal ions. The metal ions form complexes with the pyrocatecholic products. This method increases the yield of pyrocatecholic products. In particular, the method of the instant invention can be used to increase the yield of L-DOPA, a drug used in the treatment of Parkinson's disease.

13 Claims, No Drawings

PREPARATION OF PYROCATECHOLIC COMPOUNDS

FIELD OF THE INVENTION

The instant invention relates to a novel method for preparing pyrocatecholic compounds, which comprises reacting monophenolic compounds with oxygen in the presence of monophenol monooxygenase and metal ions under suitable reaction conditions. The pyrocatecholic products are stabilized through formation of complexes between the pyrocatecholic products and the metal ions.

BACKGROUND OF THE INVENTION

The pyrocatecholic compound L-DOPA is useful in treating Parkinson's disease. Other pyrocatecholic compounds are useful in photography, dyeing processes, and as chemical reagents and pharmaceuticals.

It is known that monophenolic compounds can be converted into pyrocatecholic compounds via a reaction catalyzed by monophenol monooxygenase (EC 1.14.18.1) (also known as tyrosinase). Various methods for preparing these pyrocatecholic compounds use tyrosinases extracted from plants, animals (Evans, W. C., Biochem, J. 31, 2155 (1937)) and a variety of microorganisms (U.S. Pat. No. 3,671,397). These methods, however, result in low yields of pyrocatecholic compounds. The main reasons for this low yield can be explained by considering the following reaction pathway:

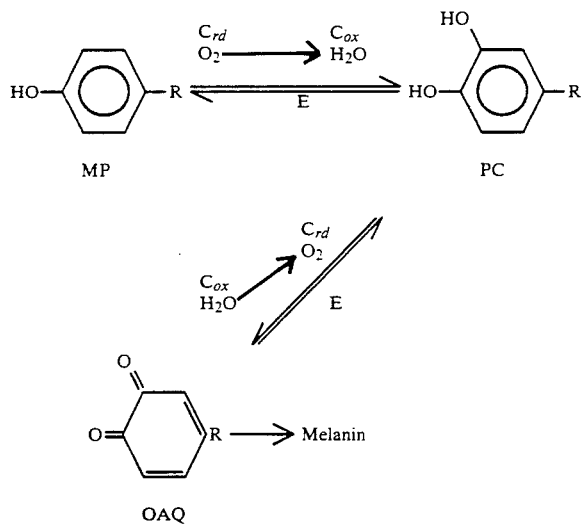

Where:
- E = monophenol monooxygenase
- MP = monophenolic compound
- PC = pyrocatecholic compound
- OAQ = orthoanthraquinone
- $C_{rd}$ = Reducing agent, reduced form
- $C_{ox}$ = Reducing agent, oxidized form In the first reaction, monophenolic compounds are oxidized to form pyrocatecholic products under the catalytic action of monophenol monooxygenase. However, the pyrocatecholic products formed are further oxidized, under the action of oxygen and this same monooxygenase, into an orthoanthraquinone, which undergo a series of subsequent reactions to finally form melanin. The overall results are low yields of pyrocatecholic products and complex mixtures of unwanted products. Sophisticated separation procedures are needed to purify the desired products.

Conventional methods for minimizing further oxidation of pyrocatecholic products involve:

1. Using vitamin C or sulfite as reducing agent to reduce orthoanthraquinone back into pyrocatecholic compound (W. C. Evans, Biochem. J., 31: 2162–2170 (1937).

2. Adding a protecting group to an appropriate position on the starting monophenolic compound to lower the oxidation rate of the pyrocatecholic product by the steric hindrance. For example, when tyrosine is used as the starting monophenolic compound, formyl or acetyl groups are used to protect the tyrosine amino group (F. E. Semersky, U.S. Pat. No. 3,812,009 (1974).

Although these methods are helpful to the production of pyrocatecholic compounds, they are complex and costly. More efficient methods of manufacturing pyrocatecholic compounds are needed.

BRIEF DESCRIPTION OF THE INVENTION

Accordingly, the instant invention provides a novel method for preparing pyrocatecholic compounds, which comprises reacting monophenolic compounds with oxygen in the presence of monophenol monooxygenase and metal ions under suitable conditions. By the present invention, the yield of pyrocatecholic products is increased.

The reaction mechanism involved in the method of the instant invention is illustrated in the following equation:

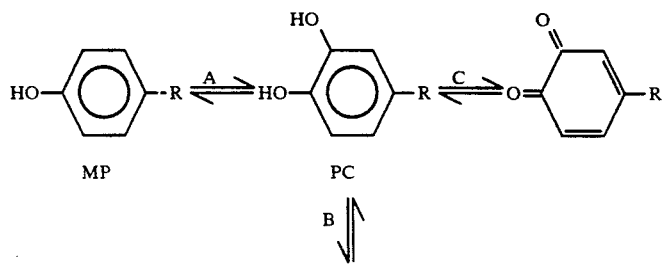

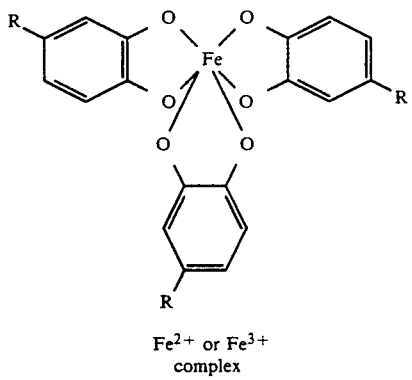

Fe$^{2+}$ or Fe$^{3+}$
complex

Reactions A and C are catalyzed by monophenol monooxygenase. It has been discovered that the pyrocatecholic product of reaction A will spontaneously form complexes (reaction B) with metal ions present in the reaction solution (e.g., Fe$^{2+}$ or Fe$^{3+}$). While not wanting to be bound by theory, it is hypothesized that the method of the present invention increases the yield of pyrocatecholic products by one or both of the following mechanisms. (1) Reaction B competes with reaction C for pyrocatecholic compound and, thereby, inhibits reaction C which leads to undesired products. (2) Reaction B also enhances the efficiency of reaction A by removing the product (PC) and shifting the equilibrium of reaction A in favor of the forward reaction.

DETAILED DESCRIPTION OF THE INVENTION

Preferred monophenolic compounds used in the instant invention are phenol, N-formyl-L-tyrosine, N-acetyl-L-tyrosine, L-tyrosine methyl ester, L-tyrosine ethyl ester, N-acetyl-L-tyrosine ethyl ester, and N-methyl-L-p-tyrosine.

Other monophenolic compounds useful in the present invention can be described in terms of the following Formulas:

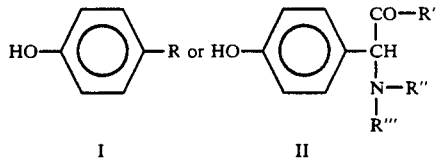

where R may be hydrogen, hydroxyl, cyclic or acyclic (C$_{1-6}$) alkyl, (C$_{2-6}$) alkenyl or C$_{2-6}$ alkynyl which include, of way of non-limiting examples, methyl, ethyl, cyclohexyl, 3-pentenyl, and 2-butynyl, heterocyclic ring system containing 3-10 carbon atoms and at least one number of N, O, or S atoms which include, of way of non-limiting examples, pyridine, pyrrolidine, piperidine, azole, oxazole, thiazole, furan, quinoline, halogen, (C$_{1-6}$) alkoxy, carboxy and its salts, (C$_{1-6}$) alkoxycarbonyl, carbamoyl, mono- and di-(C$_{1-6}$)alkylcarbamoyl, sulphamoyl, mono and di(C$_{1-6}$)alkylamino, (C$_{1-6}$) acyl, ureido, (C$_{1-6}$)alkoxycarbonyl, (C$_{1-6}$)alkoxyimino, (C$_{1-6}$)alkylthio, arylthio, (C$_{1-6}$)alkylsulphinyl, arylsulphinyl, (C$_{1-6}$)alkylsulphonyl, or arylsulphonyl; R' may be hydroxyl, (C$_{1-6}$)alkoxy, (C$_{1-6}$)alkyl, or heterocyclic ring system containing 3-10 carbon atoms and at least one member of N, O, or S atoms; R'' may be hydrogen and cyclic or acyclic (C$_{1-6}$)alkyl; and where R''' may be hydrogen, cyclic or acyclic (C$_{1-6}$) alkyl, (C$_{1-6}$)acyl, (C$_{1-6}$)alkylsulphinyl, arylsulphinyl, (C$_{1-6}$)alkylsulphonyl, or arylsulphonyl, or an amino protecting group such as, by way of non-limiting examples, t-butyl, 1-methylcyclohexyl-, benzyl-, or ethylacetoacetyl.

Monophenol monooxygenase enzyme can be prepared from a number of sources including mushroom, potato, bran, mealworm, frog epidermis, and microorganisms. For use in the present invention, the enzyme need not be extensively purified. The enzyme may be prepared by homogenizing the enzyme source in ammonium sulfate (20% of saturation) to extract the enzyme. The enzyme extract is then partially purified by adding ammonium sulfate to 70% of saturation to precipitate the monooxygenase.

More extensive enzyme purifications are known (Podila, G. K., Biochem, Biophys. Res. Commun. 141:697 (1986)), incorporated herein by reference). Highly purified enzyme preparations may prove useful in the practice of the present invention and are within the scope of the present invention.

In general, between about 1 U and about 10 U of enzyme (one unit converts 1 umoles/hr under optimal conditions) are added for each mg of monophenolic starting material.

In principle, the monooxygenase enzyme requires the presence of a reducing agent to maintain the active, reduced form of the enzyme. Vitamin C is one of a number of reducing agents which may be added to the reaction mixture of the present invention to maintain the active form of the monooxygenase enzyme. Other such reducing agents include derivatives of vitamin C, sulfite and thiosulfate salts. In addition, these reducing agents can convert orthoanthraquinones back to the corresponding pyrocatecholic compounds and further enhance the yield of pyrocatecholic compounds.

The metal ions used in the instant invention comprise iron ions, Fe$^{+2}$ or Fe$^{+3}$, and other metal ions which can form complexes with pyrocatecholic compounds. Such metal ions which may be used include Mn$^{+2}$, Ni$^{+2}$, Co$^{+2}$, Al$^{+3}$, and Zn$^{+2}$.

The amount of metal ion added to the reaction mixture is generally from about 0.1 to 2 mole per mole of the pyrocatecholic compound generated. Preferably, the amount of metal added is about 0.33 to 1 mole per mole of the pyrocatecholic compound generated.

It has been discovered that the complexes between pyrocatecholic compounds and the metal ions form when the pH is from 4 to 11, preferably from 6 to 10. Accordingly, the reaction in the instant invention is preferably carried out in a aqueous buffer solution suitable for maintaining such a pH. Suitable buffer solutions include aqueous solutions of phosphate, borate, carbonate, triethanolamine-HCl and 2-amino-2-hydroxymethyl-1,3-propanediol-HCl. The buffer concentration is generally 0.01M to 0.2M. The reaction temperature is in a range of 0° C. to 60° C., preferably 4° C. to 50° C., and most preferably, 10° C. to 45° C.

The oxygen required for the operation of the method of the invention is, conveniently, supplied by atmospheric oxygen, although oxygen gas from other sources may be used. The oxygen may be mixed into the reaction mixture simply by vigorous agitation or bubbling into the reaction mixture.

The method of the present invention can be conducted batchwise, in a series of reaction vessels or in a continuous manner. For instance, the monooxygenase enzyme can be covalently attached to a solid support such as agarose or Sepharose TM (Pharmacia LKB Biotechnology, Piscataway, N.J.) or immobilized onto membranes or cross-linked matrices such polyacrylamide by a number of known techniques (e.g. Wykes, Nature, 230:187 (1970) and Leadlay, P. F. The Chemical Society Monograph for Teachers No. 32, 67 (1978)). The monophenolic compound can then be passed over the enzyme-containing solid support in the presence of buffer, metal ions, reductants and oxygen and at an appropriate temperature. In addition, the method can also be conducted in a water miscible (single phase) or immiscible (biphasic) organic co-solvent system (Findeis, M. A. et al. Ann. Rep. in Med. Chem. 19, 263 (1984)). Reaction times in a batchwise process are generally between about 1 hr. and about 10 hrs., preferably between about 3 hrs. and about 5 hrs. Appropriate residence times for a continuous process can be estimated from the batchwise data and optimized by normal experimentation.

The pyrocatecholic product of the present invention can be isolated by standard chemical methods, including crystallization and chromatography, as the metal ion salt. The pyrocatecholic product can also be separated from the metal ions by a variety of methods, including, the addition of hydrogen sulfide.

The method of the instant invention increases the yield of pyrocatecholic product and simplifies the manufacturing process. The method, thus, lowers the cost of manufacturing pyrocatecholic compounds.

The instant invention will be illustrated substantially by the following non-limiting examples.

EXAMPLE 1

An monooxygenase enzyme was prepared by homogenizing 50 grams of fresh mushrooms, 200 ml water and 20 gram ammonium sulfate in a Waring blender. The homogenate was centrifuged at 4° C., 10,000×g for 30 minutes to remove debris, such as fiber. To the supernatant, 100 gram of ammonium sulfate were added and the supernatant was stirred at 4° C. for 12 hours to precipitate the monophenol monooxygenase enzyme. The precipitate was recovered by centrifugation (as above) to yield about 5 gram of a monophenol monooxygenase-containing preparation.

A reaction mixture was formed by dissolving 0.5 gram of the monooxygenase enzyme preparation in 10 ml 0.1M phosphate buffer, pH 7, and adding 0.045 gram L-tyrosine, 0.1 gram vitamin C, and 0.022 gram ferric chloride. The reaction mixture was placed in a 35° C. water bath (shaking at 120 rpm) for 3 hours. The results, in Table 1, show a significant increase in the yield of the product, L-DOPA, using the method of the instant invention when compared with the method without adding ferric ion, When a reducing agent is added to this system the OAQ is quickly reduced to PC. Because the bioconversion reaction was stopped before reducing agent was used up, most of the compounds left in solution were MP and PC.

TABLE 1

|  | L-Tyrosine reactant (mg) | L-DOPA (mg) | Residual L-tyrosine (mg) |
|---|---|---|---|
| Control (no $Fe^{+3}$) | 45 | 13.1 | 31.7 |
| The instant method | 45 | 25.0 | 20.1 |

EXAMPLES 2-8

Examples 2-8 repeat the procedure in Example 1 except L-tyrosine was replaced with the corresponding monophenolic compound listed in Table 2. The results, in Table 2, reveal that the yields of the corresponding pyrocatecholic products (yield = 100% X moles pyrophenolic/ moles monophenolic in the starting mixture) are about 3% to 110% higher than that of control.

TABLE 2

| Example | Monophenolic reactant | Percent increase of yield (%) |
|---|---|---|
| 2 | phenol | 9.2 |
| 3 | N-formyl-L-tyrosine | 13.9 |
| 4 | N-acetyl-L-tyrosine | 3.6 |
| 5 | L-tyrosine methyl ester | 16.8 |
| 6 | L-tyrosine ethyl ester | 25.8 |
| 7 | N-acetyl-L-tyrosine ethyl ester | 106.4 |
| 8 | N-methyl-L-p-tyrosine | 64.1 |

EXAMPLE 9

The procedure described in Example 1 was followed except that monophenol monooxygenase was extracted from potato. The results are shown in Table 3, where the yield increasing effect of iron ion is again significant.

TABLE 3

|  | L-Tyrosine reactant (mg) | L-DOPA (mg) | Residual L-tyrosine (mg) |
|---|---|---|---|
| Control (no $Fe^{+3}$) | 55 | 9.4 | 24.2 |
| The instant method | 55 | 17.0 | 24.0 |

EXAMPLE 10

The procedure described in Example 1 was followed except that borate buffer (0.05M, pH 8.0) was used instead of phosphate buffer. The results are shown in Table 4.

TABLE 4

|  | L-Tyrosine reactant (mg) | L-DOPA (mg) | Residual L-tyrosine (mg) |
|---|---|---|---|
| Control (no $Fe^{+3}$) | 60 | 18.8 | 33.5 |
| The instant method | 60 | 23.9 | 25.4 |

EXAMPLE 11 .

The procedure described in Example 1 was followed except that carbonate buffer (0.05M, pH 7.0) was used instead of phosphate buffer. The results are shown in Table 5.

TABLE 5

| | L-Tyrosine reactant (mg) | L-DOPA (mg) | Residual L-tyrosine (mg) |
|---|---|---|---|
| Control (no $Fe^{+3}$) | 55 | 13.5 | 34.3 |
| The instant method | 55 | 14.7 | 30.4 |

EXAMPLE 12

The procedure described in Example 1 was followed except that triethanolamine-HCl (0.05M, pH 7.0) buffer was used instead of phosphate buffer. The results are shown in Table 6.

TABLE 6

| | L-Tyrosine reactant (mg) | L-DOPA (mg) | Residual L-tyrosine (mg) |
|---|---|---|---|
| Control (no $Fe^{+3}$) | 55 | 12.4 | 33.3 |
| The instant method | 55 | 15.3 | 31.6 |

EXAMPLE 13

The procedure described in Example 1 was followed except that Tris (hydroxymethyl) aminomethane (TRIS) buffer (0.05M, pH 7.0) was used instead of phosphate buffer. The results are shown in Table 7.

TABLE 7

| | L-Tyrosine reactant (mg) | L-DOPA (mg) | Residual L-tyrosine (mg) |
|---|---|---|---|
| Control (no $Fe^{+3}$) | 55 | 17.8 | 32.2 |
| The instant method | 55 | 20.6 | 30.5 |

Additional experiments using buffers such as acetic, citric, succinic and phthalate buffer have shown that as long as the pH was in the range of 4 to 11, a complex between the iron ion and the pyrocatecholic products would form and stabilize the pyrocatecholic products.

What is claimed is:

1. A method for preparing pyrocatecholic compounds comprising reacting monophenolic compounds with an oxygen-containing gas in an aqueous solution having a pH between about 4 and about 11 in the presence of monophenol monooxygenase and a metal ion capable of forming a complex with the pyrocatecholic compounds, said metal ion being present in a concentration between about 0.1 and about 2 moles per mole of pyrocatecholic compound.

2. The method according to claim 1, wherein the monophenol monooxygenase is obtained by extracting and separating an enzyme source selected from mushrooms, potatoes, bran, mealworm, frog epidermis and microorganisms.

3. The method according to claim 1, wherein said monophenolic compound is phenol, L-tyrosine, N-formyl-L-tyrosine, N-acetyl-L-tyrosine, L-tyrosine methyl ester, L-tyrosine ethyl ester, N-acetyl-L-tyrosine ethyl ester or N-methyl-L-p-tyrosine.

4. The method according to claim 1, wherein said metal ion is a $Fe^{+2}$, $Fe^{+3}$, $Mn^{+2}$, $Ni^{+2}$, $Co^{+2}$, $Al^{+3}$ or $Zn^{+2}$.

5. The method according to claim 4, wherein said metal ion is $Fe^{+2}$ or $Fe^{+3}$.

6. The method according to claim 1, wherein the reaction takes place in the presence of a reducing agent capable of reducing an orthoanthraquinone to its corresponding pyrocatecholic compound.

7. The method according to claim 6, wherein said reducing agent is a sulfite salt, a thiosulfate salt, vitamin C or a derivative of vitamin C.

8. The method according to claim 1, wherein said aqueous solution is buffered with an acetate, citrate, succinate, phthalate, phosphate, borate, carbonate, triethanolamine-HCl or Tris (hydroxymethyl) aminomethane buffer.

9. The method according to claim 8, wherein said pH is in the range of about 6 to about 10.

10. The method according to claim 1, wherein the reaction temperature is in the range of 0° C. to 60° C.

11. The method according to claim 10, wherein the reaction temperature is in the range of 4° C. to 50° C.

12. The method according to claim 11, wherein the reaction temperature is in the range of 10° C. to 45° C.

13. The method according to claim 1, wherein the metal ion concentration is between about 0.33 to 1 mole per mole of pyrocatecholic compound.

* * * * *